(12) United States Patent
Liang

(10) Patent No.: US 7,275,826 B2
(45) Date of Patent: Oct. 2, 2007

(54) FUNDUS CAMERA HAVING CURVED MIRROR OBJECTIVE

(75) Inventor: Rongguang Liang, Penfield, NY (US)

(73) Assignee: Carestream Health, Inc., Rochester, NY (US)

( * ) Notice: Subject to any disclaimer, the term of this patent is extended or adjusted under 35 U.S.C. 154(b) by 314 days.

(21) Appl. No.: 11/196,227

(22) Filed: Aug. 3, 2005

(65) Prior Publication Data

US 2007/0030449 A1 Feb. 8, 2007

(51) Int. Cl.
*A61B 3/14* (2006.01)
*A61B 3/00* (2006.01)

(52) U.S. Cl. ...................... 351/206; 351/221
(58) Field of Classification Search ............... 351/205, 351/206, 221
See application file for complete search history.

(56) References Cited

U.S. PATENT DOCUMENTS

| 4,247,176 | A | 1/1981 | Ito |
| 4,838,680 | A | 6/1989 | Nunokawa |
| 5,198,845 | A * | 3/1993 | Triller .................... 351/221 |
| 5,233,372 | A * | 8/1993 | Matsumoto ............... 351/221 |
| 5,499,139 | A | 3/1996 | Chen et al. |
| 5,572,266 | A | 11/1996 | Ohtsuka |
| 5,713,047 | A | 1/1998 | Kohayakawa |
| 5,742,374 | A | 4/1998 | Nanjo et al. |
| 5,847,805 | A | 12/1998 | Kohayakawa et al. |
| 5,889,625 | A | 3/1999 | Chen et al. |
| 5,943,116 | A | 8/1999 | Zeimer |
| 6,296,358 | B1 | 10/2001 | Cornsweet et al. |
| 6,546,198 | B2 | 4/2003 | Ohtsuka |
| 6,585,374 | B2 | 7/2003 | Matsumoto |
| 6,636,696 | B2 | 10/2003 | Saito |

* cited by examiner

*Primary Examiner*—Scott J. Sugarman

(57) ABSTRACT

An apparatus (50) for obtaining an image of the eye, has a light source (114) for providing an incident illumination and an apertured mirror (104) for directing at least a portion of the incident illumination along an optical axis. A curved objective mirror (102) directs the incident illumination received along the optical axis toward the retina of the eye and directs image-bearing light reflected from the retina back along the optical axis. The apertured mirror (104) transmits the image-bearing light reflected from the retina toward a sensor (108) for obtaining an image of the retina thereby.

10 Claims, 9 Drawing Sheets

FUNDUS CAMERA HAVING CURVED MIRROR OBJECTIVE

FIELD OF THE INVENTION

This invention generally relates to electronic imaging apparatus for fundus imaging and more particularly relates to an improved fundus imaging apparatus using a curved mirror objective for forming an image of the eye.

BACKGROUND OF THE INVENTION

Fundus camera imaging is acknowledged to be an important diagnostic tool for detection of various conditions affecting the eye, including diabetic retinopathy and macular degeneration. Various embodiments of fundus imaging apparatus are disclosed, for example in U.S. Pat. No. 5,713,047 (Kohayakawa); U.S. Pat. No. 5,943,116 (Zeimer); U.S. Pat. No. 5,572,266 (Ohtsuka); U.S. Pat. No. 4,838,680 (Nunokawa); U.S. Pat. No. 6,546,198 (Ohtsuka); U.S. Pat. No. 6,636,696 (Saito); U.S. Pat. No. 4,247,176 (Ito); U.S. Pat. No. 5,742,374 (Nanjo et al.); and U.S. Pat. No. 6,296,358 (Cornsweet et al).

While these patents attest to continuous improvements in fundus camera design, there are still significant hurdles to obtaining good quality images from these devices. Fundus cameras must solve the fairly difficult problem of simultaneously illuminating the retina through the pupil and obtaining the retinal image, with both illumination and image-bearing light traveling along substantially the same optical path. One particularly troublesome problem relates to stray light caused by unwanted reflection from the lens surface of the patient's eye itself as well as from optical surfaces within the camera apparatus. Unless its level is controlled, this unwanted reflected light can degrade image contrast and overall image quality.

This problem is most readily illustrated by an overview of the operation of the illumination subsystem in a conventional fundus imaging apparatus. Referring to FIG. 1, there is shown a fundus imaging apparatus 10 in which a conventional illumination section 12 is used. The patient's eye E is positioned along an optical axis O using an alignment subsystem (not shown in FIG. 1). Illumination section 12 directs light either from an observation light source 14 and a lens 16 or from an image capture light source 18 and a lens 20 as controlled by control logic circuitry for fundus imaging apparatus 10 (not shown in FIG. 1). A dichroic mirror 22 directs light from the appropriate source through a ring-slit diaphragm 24 and a lens 26, to an apertured mirror 28. Apertured mirror 28 directs the illumination light along axis O and through an objective lens 42 toward the pupil for illuminating the retina of eye E. Depending on the use of fundus imaging apparatus 10 at any one time, either observation light source 14 or image capture light source 18 are activated. Observation light source 14 is typically infrared (IR) light, to which eye E is insensitive. Image capture light source 18, on the other hand, may be a high-brightness source such as a xenon lamp, for example. Depending on the application, image capture light source 18 may be pulsed or strobed.

Ring-slit diaphragm 24 has the characteristic functional arrangement shown in FIG. 2. Light is transmitted through an inner ring 30 and is blocked at a middle section 32 and at an outer section 34. As is shown in the received illumination ring of FIG. 3, inner ring 30 is directed into a pupil 36 of the patient as a ring 40 of illumination. To obtain the retinal image, apertured mirror 28 (FIG. 1) has an aperture suitably centered about optical axis O to allow light that has been reflected from the retina of eye E and directed through lenses 42 and 44 to reach a sensor 46, such as a CCD.

The high-level block diagram of FIG. 1 thus gives an overview of illumination section 12 that applies for conventional fundus imaging apparatus. There have been numerous methods disclosed for optimizing the performance of illumination section 12, including components arranged to prevent stray reflected light from the cornea of eye E and from optical surfaces from being directed back toward sensor 46. Referring to the schematic block diagram of FIG. 1, three basic approaches have been followed in order to reduce or eliminate stray light from these sources:

(i) Using a pair of crossed polarizers. Using this approach, a first polarizer 600 is placed in the illumination path, prior to apertured mirror 28. A second polarizer 602 is then positioned in the image path, following apertured mirror 28. With reference to FIG. 1, first polarizer 600 and second polarizer 602 are positioned as shown at phantom locations. The polarizers 600 and 602 are cross-aligned so that the light reflected back from the lens surfaces can be blocked by polarizer 602.

There are two key problems with this method. The first problem relates to the needed high power lamp when using this strategy. Because only that portion of light having the proper polarization is transmitted through polarizer 600, more light is needed from image capture light source 18. The use of second polarizer 602 further blocks the useful light reflected from the retina by 50%. As a result, the power of light source 18 must be about 4 times as high as would be necessary without polarizers 600 and 602. The second problem relates to the nature of light reflected from the cornea. Since this light can be depolarized, particularly due to the large incident angle, second polarizer 602 will be less effective in blocking unwanted stray light.

(ii) In the illumination path, blocking reflected light which, otherwise, will reflect from the lens surface and reach the sensor 46. This solution, however, reduces uniformity of the desired light reflected from the retina, particularly noticeable when attempting to obtain retinal images from near-sighted patients.

(iii) Separating illumination and imaging optical paths. A beamsplitter can be placed in front of objective lens 42 to effect this separation. However, this type of solution requires additional light power in order to obtain suitable reflected light from the retina and necessitates a longer working distance for objective lens 42.

Reflective optics have been used in display apparatus that require a highly compact optical arrangement. For example, U.S. Pat. No. 5,889,625 (Chen et al.) discloses an optical arrangement that directs an image-bearing light to a human observer using a curved mirror as part of a head-mounted device (HMD). Similarly, U.S. Pat. No. 5,499,139 (Chen et al.) discloses a helmet-mounted optical apparatus for providing a wide-field image to a pilot, where the optical apparatus employs a curved mirror and compensation for image aberration. However, while mirrors have been used effectively in display applications of this type, the use of curved mirrors in a system that must simultaneously illuminate and capture an image is understandably much more difficult.

Mirrors have also been utilized in some more complex ophthalmological cameras for imaging internal structures of the eye. For example, U.S. Pat. No. 5,847,805 (Kohayakawa et al.) discloses an apparatus for scanning a pair of beams into the eye using a combination of rotary polygon scanning mirror and a galvanometric mirror. Similarly, U.S. Pat. No. 6,585,374 (Matsumoto) discloses various embodiments using a movable concave mirror mounted on a rotation axis for imaging different portions of the eye from different rotated positions. The apparatus of U.S. Pat. Nos. 5,847,805 and 6,585,374 are relatively costly, high-end ophthalmological imaging devices that require added movable components in the optical path in order to obtain multiple images for diagnosis.

There is a need for inexpensive fundus imaging cameras where scanning operation is not needed. This less complex type of camera is designed for use in physician's offices and is used for first-level screening for diabetic retinopathy, for example. With such an apparatus, a single retinal image from each eye is all that is needed for screening.

In summary, there is a need for a lower cost optical system in a fundus imaging camera that reduces stray light from lens surface reflection without significantly increasing the needed illumination brightness and without adversely affecting image quality.

SUMMARY OF THE INVENTION

Briefly, according to one aspect of the present invention an apparatus for obtaining an image of the retina of the eye comprises:
  a) a light source for providing an incident illumination;
  b) an apertured mirror for directing at least a portion of the incident illumination along an optical axis;
  c) a curved objective mirror for directing the incident illumination received along the optical axis toward the retina of the eye and for directing image-bearing light reflected from the retina back along the optical axis;
  wherein the apertured mirror transmits the image-bearing light reflected from the retina toward a sensor; and
  the sensor obtaining an image of the retina thereby.

It is a feature of the present invention that it provides a fundus imaging apparatus with a mirror that acts as the objective lens.

It is an advantage of the present invention that it minimizes stray reflected light from the surfaces of lenses as well as from other optical components in the imaging path.

These and other objects, features, and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

While the specification concludes with claims particularly pointing out and distinctly claiming the subject matter of the present invention, it is believed that the invention will be better understood from the following description when taken in conjunction with the accompanying drawings, wherein:

DETAILED DESCRIPTION OF THE INVENTION

The present description is directed in particular to elements forming part of, or cooperating more directly with, apparatus in accordance with the invention. It is to be understood that elements not specifically shown or described may take various forms well known to those skilled in the art.

Figure 1:
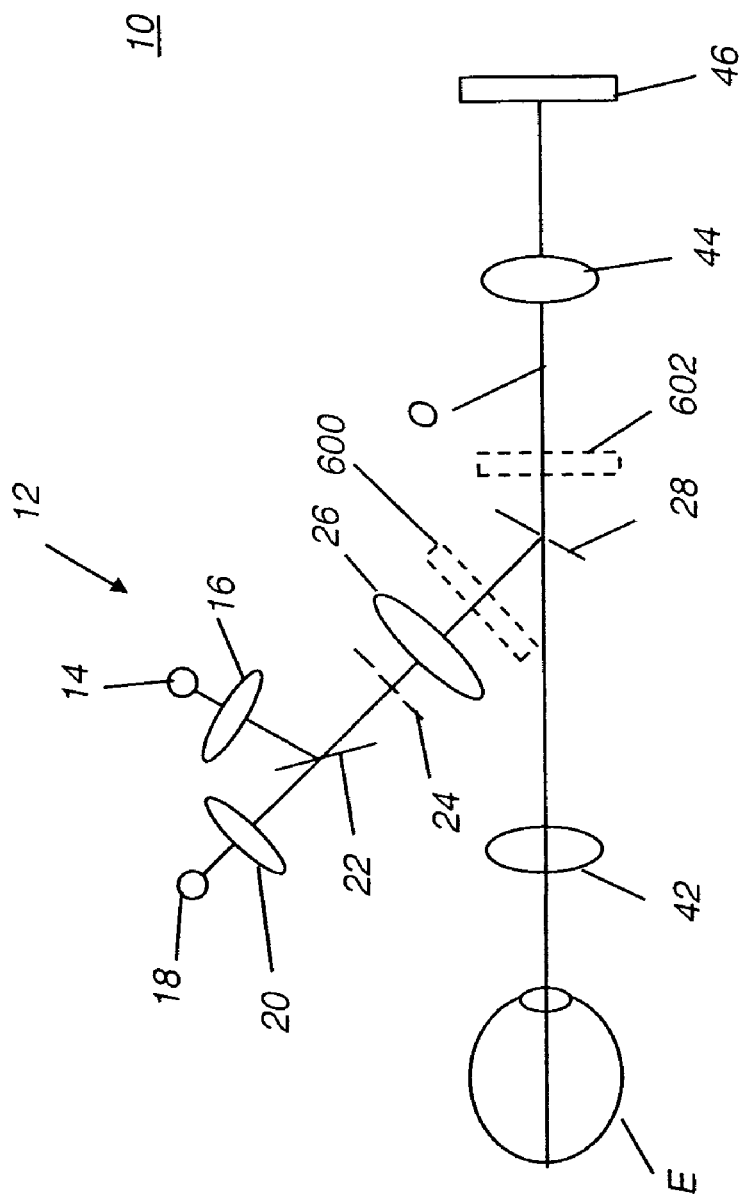
FIG. 1 is a schematic block diagram showing a conventional arrangement of illumination and imaging optics in a fundus imaging apparatus.
Figure 2:
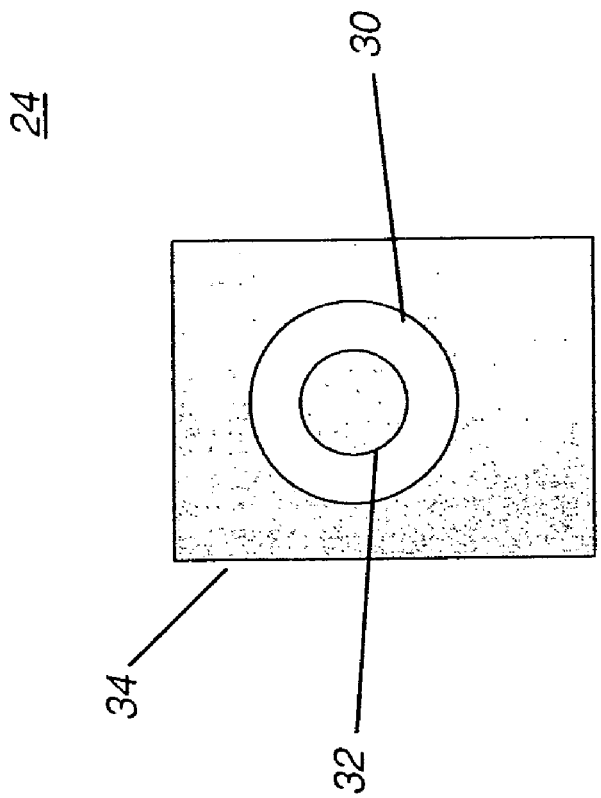
FIG. 2 is a plan view of a ring-slit diaphragm used in a conventional fundus imaging apparatus.
Figure 3:
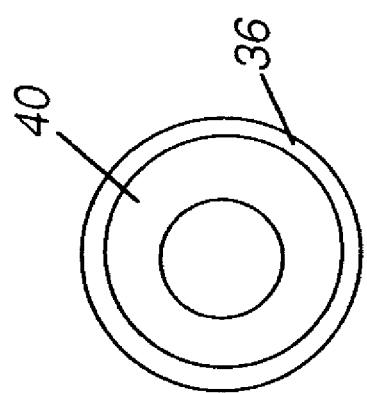
FIG. 3 is a plan view representation of the ring of illumination applied to the pupil of a patient in a conventional apparatus.
Figure 4:
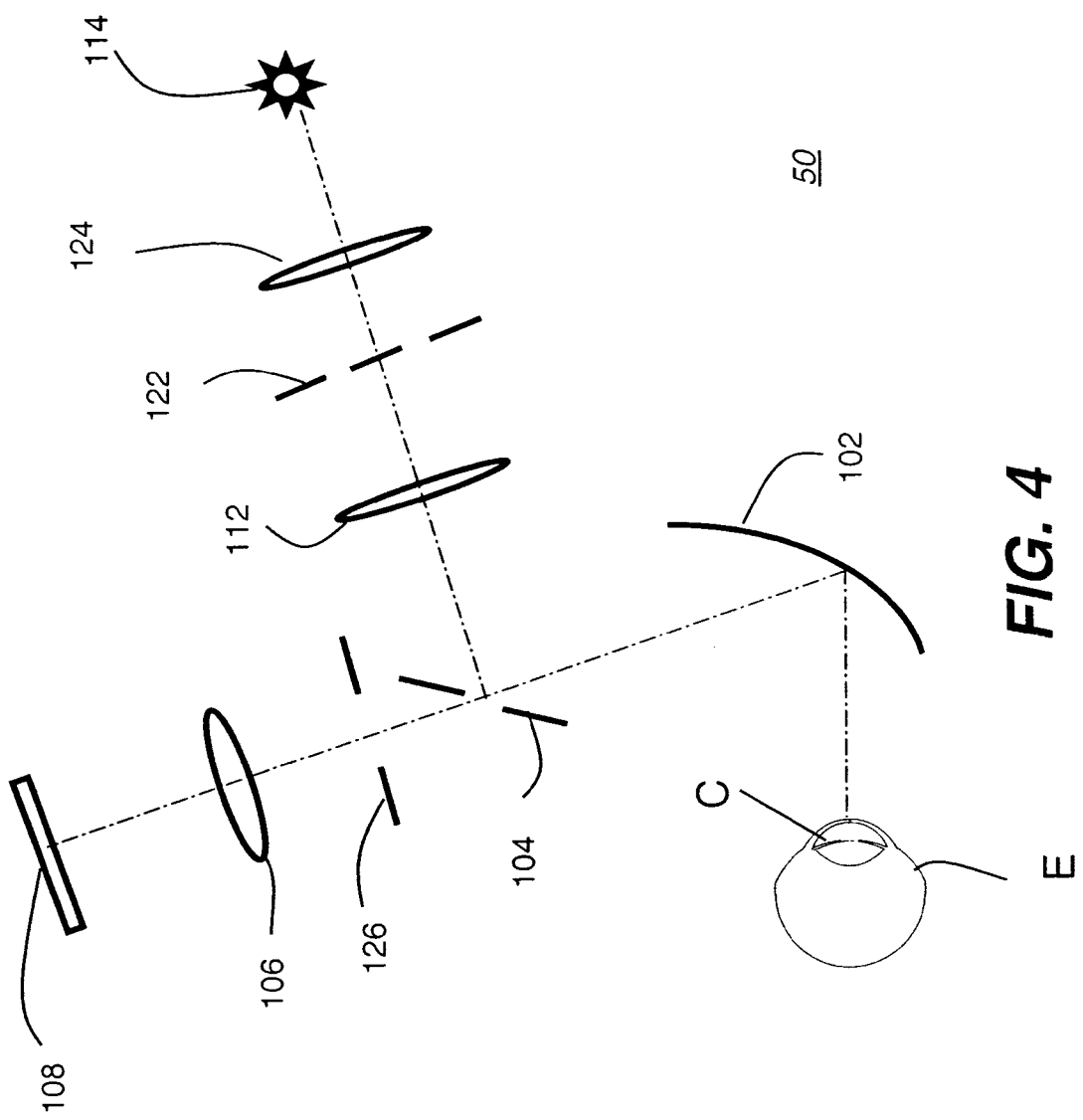
FIG. 4 is a schematic block diagram showing the overall arrangement of imaging components in a fundus imaging apparatus of the present invention.

Referring to FIG. 4, there is shown a block diagram of illumination and imaging components of a fundus imaging apparatus 50 in a first embodiment of the present invention. An imaging light source 114 provides imaging illumination through lenses 124 and 112 and through a ring-slit diaphragm 122 to an apertured mirror 104. This illumination is then directed into eye E by a curved mirror 102. Curved mirror 102 is off-axis and serves as the objective lens in this embodiment. This arrangement eliminates back-reflection from the objective lens, such as from lens 42 in FIG. 1. Curved mirror 102 is toroidal in one embodiment, rather than spherical, to minimize third-order astigmatism, commonly introduced by off-axis mirrors. A concave elliptical mirror could also be advantageous.

In order to minimize third-order astigmatism, the principal radii in x- and y-directions, $R_x$ and $R_y$, respectively, must meet the Coddington equations, as follows:

$$\frac{1}{t} + \frac{1}{t'} = \frac{2}{R_y \cos\theta} \quad (1)$$

$$\frac{1}{s} + \frac{1}{s'} = \frac{2\cos\theta}{R_x} \quad (2)$$

where t, s, t', and s' are the distance along the rays from the astigmatism focal surface to the focus from the object and image distance, respectively, and $\theta$ is the angle of the mirror with respect to the optical axis.

With the eye properly aligned, the light reflected from the retina is substantially at infinity; thus, values $$\frac{1}{t} \text{ and } \frac{1}{s}$$

are zero. Thus:

$$R_x = R_y (\cos\theta)^2$$

Ring-slit diaphragm 122, apertured mirror 104, and the cornea C of eye E are optically conjugate. The ring of illumination is sizeable enough so that light reflected back from the cornea is blocked by apertured mirror 104 and by a stop aperture 126. Only the image light is directed toward a sensor 108 by a camera lens 106.

Figure 5:
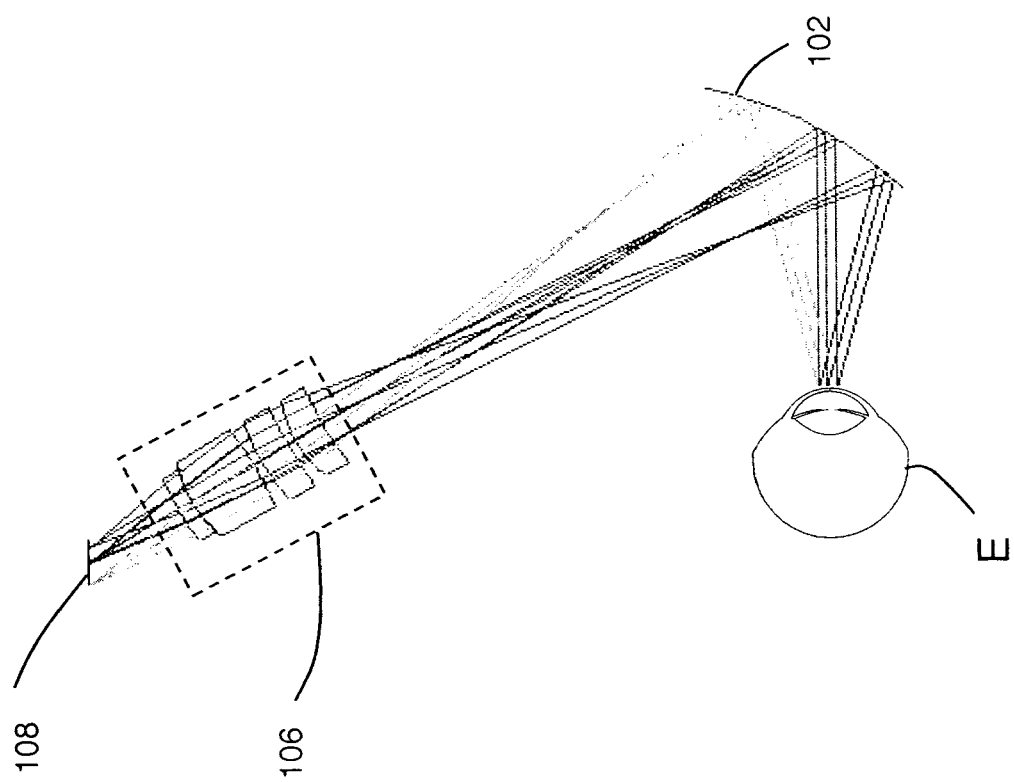
FIG. 5 is a diagram showing the path of imaging light in one embodiment.

The basic arrangement of FIG. 4 can be implemented in a number of ways. For example, referring to FIG. 5, there is shown a ray diagram of camera lens 106 in one embodiment. This design utilizes a symmetric refractive lens. In order to minimize aberration from curved mirror 102 such as coma and astigmatism, sensor 108 is tilted relative to lens 106.

Figure 6:
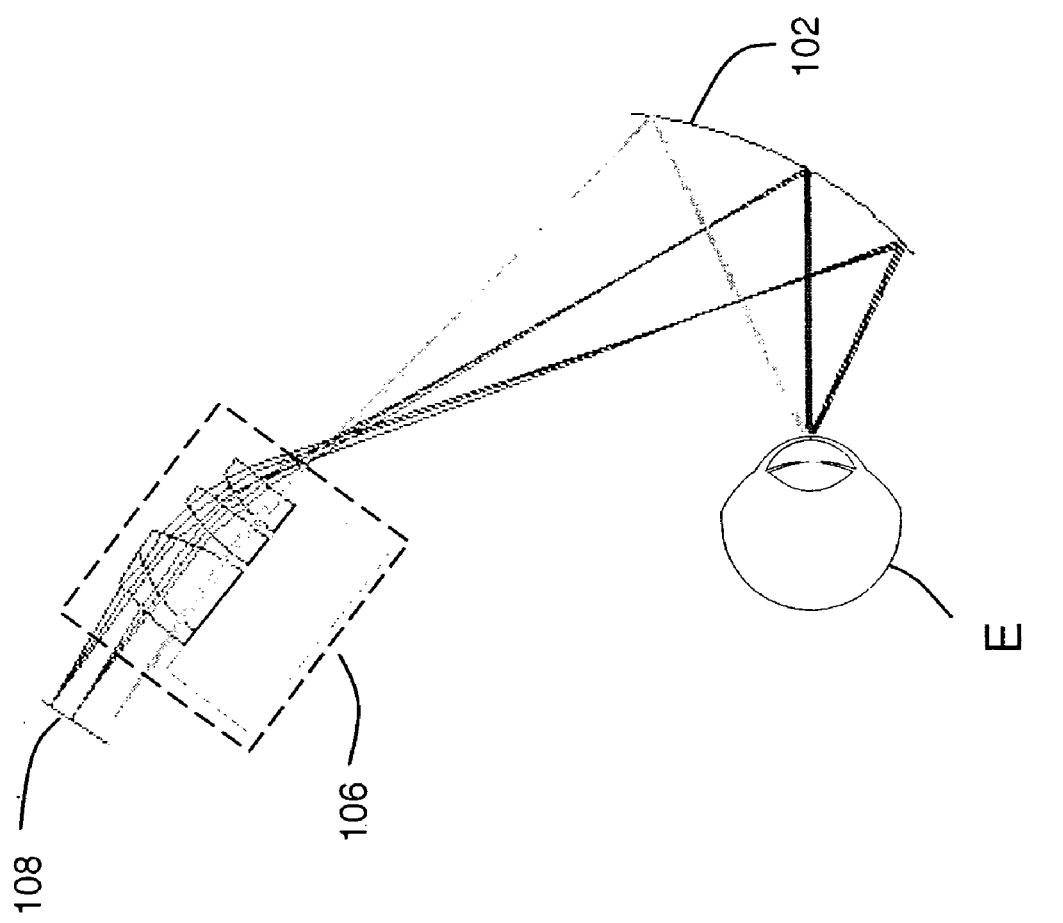
FIG. 6 is a diagram showing the path of imaging light in an alternate embodiment.

The alternate arrangement of FIG. 6 shows a ray diagram of camera lens 106 in another embodiment. Here, lens 106 is decentered to compensate for mirror aberration. With such an arrangement, it can be difficult to correct for distortion; however, digital techniques can be employed to correct for distortion in fundus imaging apparatus 50.

Figure 7:
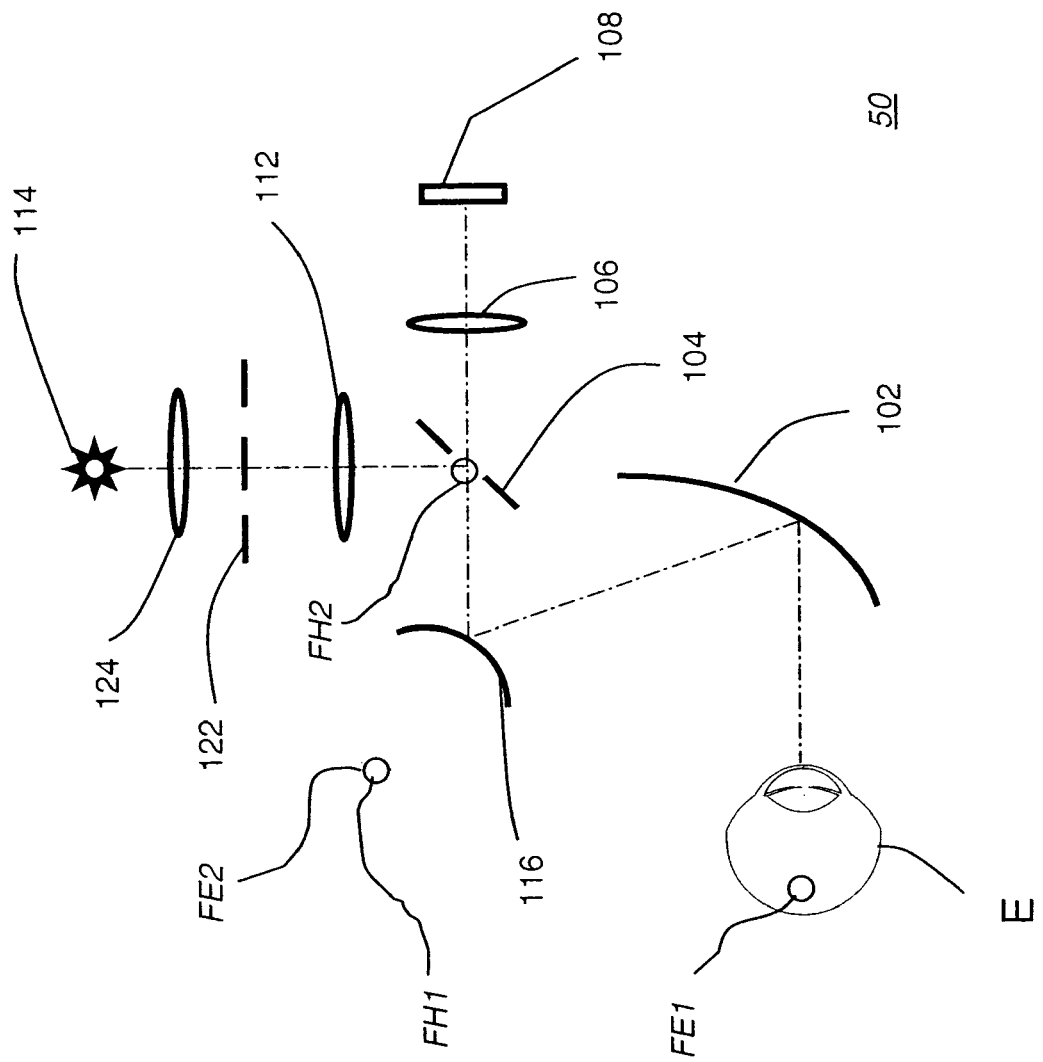
FIG. 7 is a schematic block diagram showing the overall arrangement of imaging components in a fundus imaging apparatus of an alternate embodiment.

Referring to FIG. 7, there is shown another embodiment of fundus imaging apparatus 50 in which a pair of mirrors is utilized to minimize aberration. A second curved mirror 116 is used to direct illumination from apertured mirror 104 and to direct image-bearing light through apertured mirror 104 to sensor 108.

The arrangement of FIG. 7 can be advantageous for reducing distortion, where mirrors 102 and 116 are carefully selected. In one embodiment, a combination is used in which mirror 102 is an ellipsoid and second curved mirror 116 is hyperboloid. For an ellipsoid shape in Cartesian x,y,z space, the basic equation is as follows:

$$\frac{x^2 + y^2}{a^2} + \frac{z^2}{b^2} = 1 \quad (3)$$

and $a^2 - b^2 = c^2$. Parameters a, b, and c are as represented in the diagram of FIG. 8A for an ellipse 200. Ellipse 200 has two focal points FE1 and FE2. An ellipsoid shape is a type of quadric shape generated by rotation of the ellipse about the axis between its focal points, the major axis.

Figure 8B:
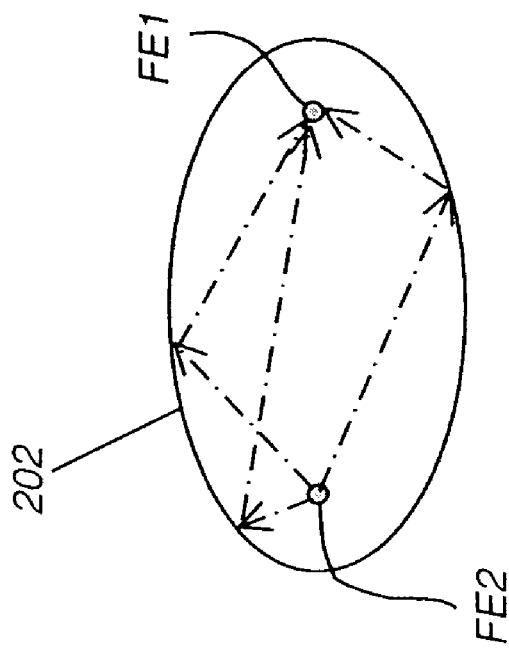
FIG. 8B is a cross-sectional diagram showing behavior of an elliptical mirror.
Figure 8A:
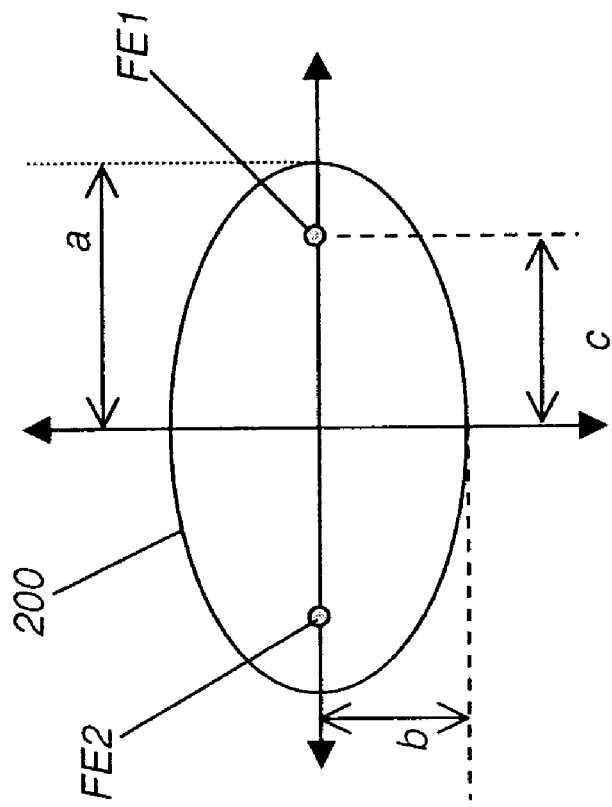
FIG. 8A is a diagram showing structure and focal points for an ellipse.

FIG. 8B shows the behavior of an elliptical mirror 202, that is, a mirror having ellipsoid shape. Light emanating from one focal point FE1 is reflected toward the other focal point FE2.

For a hyperboloid shape in Cartesian x,y,z space, the basic equation is as follows:

$$\frac{x^2 + y^2}{a^2} - \frac{z^2}{b^2} = 1 \quad (4)$$

and $a^2 + b^2 = c^2$. Parameters a, b, and c for an hyperbola 300 are as represented in the diagram of FIG. 9A. Hyperbola 300 has two focal points, FH1 and FH2. A hyperboloid shape is a type of quadric shape that can be generated by rotation of the hyperbola about the axis between its focal points.

Figure 9B:
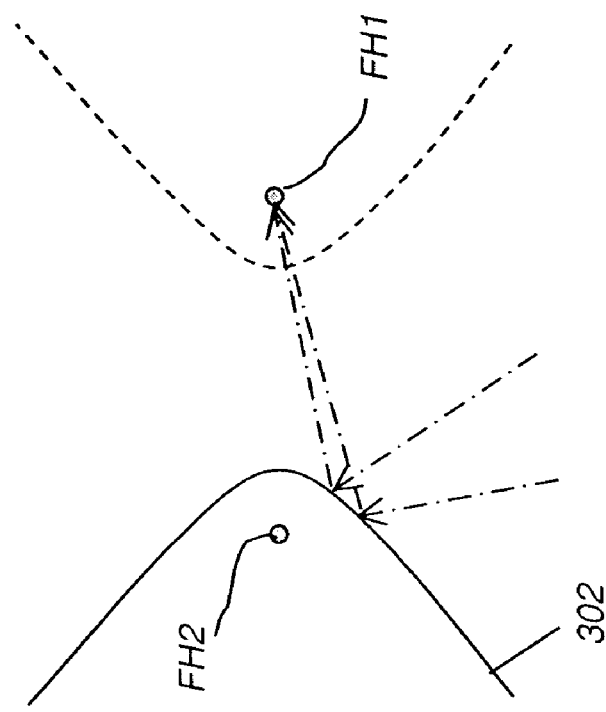
FIG. 9B is a cross-sectional diagram showing behavior of a mirror having hyperbolic shape.
Figure 9A:
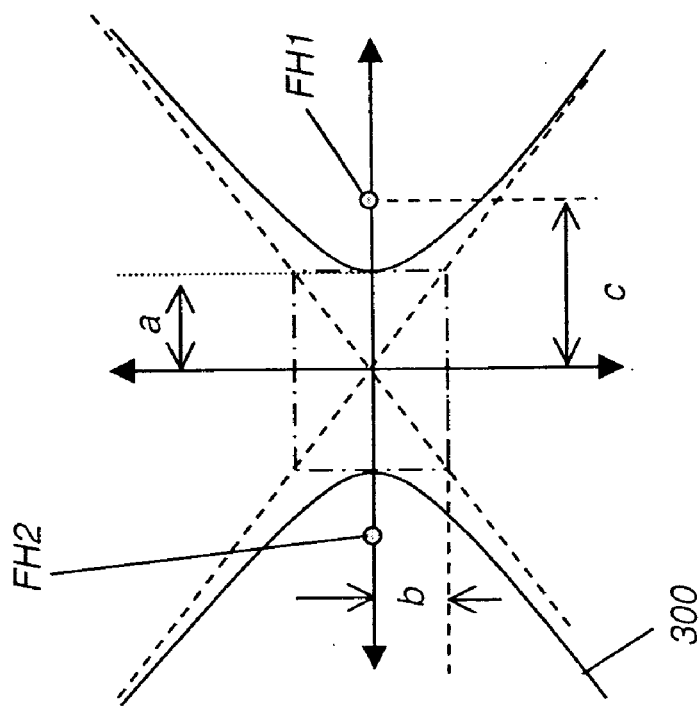
FIG. 9A is a diagram showing structure and focal points for an hyperbola.

FIG. 9B shows the behavior of a hyperbolic mirror 302, that is, a mirror having a substantially hyperboloid shape. Light rays that are directed toward one focal point FH2 are reflected toward the other focal point FH1.

FIG. 7 takes advantage of the behavior of hyperboloid and ellipsoid mirrors to reflect light from one focal point to another focal point. In operation, then, ellipsoid mirror 102 reflects light from the retina of eye E from one of its focal points FE1 (at or near the retina) toward its other focal point FE2, which is a focal point FH1 shared with hyperboloid second mirror 116. Second curved mirror 116 reflects this light to its other focal point FH2 near apertured mirror 104.

By using an ellipsoid/hyperboloid combination, distortion of curved mirror 102 is at least partially corrected by second curved mirror 116. Mirror 116 also acts as a folding mirror, allowing a more compact imaging system. For this combination of ellipsoid/hyperboloid mirrors 102 and 116 respectively, the ideal arrangement is to have focal point FE1 at or very near the lens of eye E. Focal points FE2 and FH2 should be substantially concentric. Focal point FH2 should be at the aperture of apertured mirror 104. Of course, perfect positioning would be difficult; some slight tolerance for positioning error would be necessary.

The use of curved mirror 102 as the objective optical component eliminates one cause of possible stray reflection (that is, from the surface of an objective lens 42 in FIG. 1) and provides an optical mechanism for preventing unwanted reflected light from the imaging path, while transmitting the desired reflected light that bears the retinal image.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention. For example, curved mirror 102 may be moved along the optical axis O in order to achieve better focus. Any of a number of different types of light sources could be used for observation, focus, and imaging.

Thus, what is provided is a fundus imaging apparatus using a curved mirror objective for forming an image of the eye.

PARTS LIST 10 fundus imaging apparatus
12 illumination section
14 observation light source
16 lens
18 image capture light source
20 lens
22 dichroic mirror
24 ring-slit diaphragm
26 lens
28 apertured mirror
30 inner ring
32 middle section
34 outer section
36 pupil
40 ring
42 lens
44 lens
46 sensor
50 fundus imaging apparatus
102 curved mirror
104 apertured mirror
106 lens
108 sensor
112 lens
114 light source
116 second curved mirror
122 ring-slit diaphragm
124 lens
126 stop aperture
200 ellipse
202 elliptical mirror 300 hyperboloid
302 hyperbolic mirror
600 polarizer
602 polarizer

The invention claimed is:

1. An apparatus for obtaining an image of an eye, comprising:
   a) a light source for providing an incident illumination;
   b) an apertured mirror for directing at least a portion of the incident illumination along an optical axis;
   c) a curved objective mirror for directing the incident illumination received along the optical axis toward a retina of the eye and for directing image-bearing light reflected from the retina back along the optical axis;
   wherein the apertured mirror transmits the image-bearing light reflected from the retina toward a sensor; and
   the sensor captures an image of the retina.

2. The apparatus of claim 1 wherein the curved objective mirror is toroidal.

3. The apparatus of claim 1 wherein the curved objective mirror is ellipsoidal.

4. An apparatus for obtaining an image of an eye, comprising:
   a) a light source for providing an incident illumination;
   b) an apertured mirror for directing at least a portion of the incident illumination along an optical axis;
   c) a first curved mirror for directing the incident illumination received along the optical axis toward a second curved mirror;
   d) the second curved mirror directing the incident illumination received from the first curved mirror toward a retina of the eye and directing image-bearing light reflected from the retina back toward the first curved mirror;
   wherein the apertured mirror transmits the image-bearing light reflected from the first curved mirror toward a sensor; and
   the sensor captures an image of the retina.

5. The apparatus according to claim 4 wherein the first curved mirror is hyperboloid.

6. The apparatus according to claim 4 wherein the second curved mirror is ellipsoidal.

7. The apparatus according to claim 4 wherein the second curved mirror is substantially ellipsoid and wherein the retina of the eye is positioned substantially at a first focus point of the ellipsoid shape of the second curved mirror;
   wherein the first curved mirror is substantially hyperboloid; wherein a second focus point of the second curved mirror is substantially concentric with a first focus point of the hyperboloid shape of the first curved mirror; and
   wherein the apertured mirror is disposed substantially at the same position as a second focus point of the first curved mirror.

8. A method for obtaining an image of an eye comprising:
   a) providing an incident illumination;
   b) directing at least a portion of the incident illumination toward an apertured mirror for redirection along an optical axis toward the eye;
   c) disposing a curved objective mirror for directing the incident illumination received along the optical axis toward a retina of the eye and for directing image-bearing light reflected from the retina back along the optical axis;
   whereby the apertured mirror transmits the image-bearing light reflected from the retina toward a sensor; and
   d) forming the image of the eye at the sensor.

9. The method of claim 8 wherein the step of disposing a curved objective mirror further comprises disposing a second mirror along the optical axis for redirecting illumination and image-bearing light to and from the curved objective mirror.

10. The method of claim 8 wherein the step of disposing a curved objective mirror comprises the step of disposing an ellipsoid mirror, wherein a first focal point of the ellipsoid mirror is substantially at the retina.

* * * * *